(12) United States Patent
Verhagen et al.

(10) Patent No.: US 9,295,518 B2
(45) Date of Patent: Mar. 29, 2016

(54) OPTICAL BLADE AND HAIR CUTTING DEVICE

(75) Inventors: Rieko Verhagen, Vught (NL); Robbert Adrianus Maria van Hal, St-Oedenrode (NL); Bart Willem Jan Spikker, Eindhoven (NL); Natallia Eduardauna Uzunbajakava, Eindhoven (NL); Babu Varghese, Eindhoven (NL); Paul Anton Josef Ackermans, Nuenen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 338 days.

(21) Appl. No.: 13/384,355

(22) PCT Filed: Jul. 14, 2010

(86) PCT No.: PCT/IB2010/053212
§ 371 (c)(1),
(2), (4) Date: Jan. 17, 2012

(87) PCT Pub. No.: WO2011/010246
PCT Pub. Date: Jan. 27, 2011

(65) Prior Publication Data
US 2012/0123444 A1    May 17, 2012

(30) Foreign Application Priority Data
Jul. 23, 2009  (EP) .................................... 09166194

(51) Int. Cl.
A61B 18/18  (2006.01)
A61B 18/20  (2006.01)
B26B 21/00  (2006.01)
(Continued)

(52) U.S. Cl.
CPC .................. *A61B 18/20* (2013.01); *B26B 21/00* (2013.01); *B26B 21/4081* (2013.01); *B26B 21/56* (2013.01); *B26B 21/58* (2013.01); *A61B 18/203* (2013.01); *A61B 2018/00452* (2013.01); *A61B 2018/00476* (2013.01); *A61B 2018/2272* (2013.01)

(58) Field of Classification Search
CPC .................. A61B 18/20; A61B 18/203; A61B 2018/2035; A61B 2018/00452; A61B 2018/0047; A61B 2018/2272; A61B 17/00; A61B 2017/00022; G02B 26/00; G02B 26/0816; G02B 26/0833; B26B 19/00
USPC .......... 606/9–13, 17, 18; 607/88–91; 128/898
See application file for complete search history.

(56) References Cited

U.S. PATENT DOCUMENTS 4,126,136 A   11/1978   Auth et al.
5,065,515 A   11/1991   Iderosa
(Continued)

FOREIGN PATENT DOCUMENTS

FR   2579446 A1   10/1986
JP   05323228 A   12/1993
(Continued)

*Primary Examiner* — Ahmed Farah

(57) ABSTRACT

An optical blade and a hair cutting device is configured to cut a hair near skin of a human body or animal body part. The optical blade maybe used in a hair cutting device and includes a blade body configured to guide optical radiation, and a tapered end configured to allow the optical radiation to exit the optical blade. The tapered end includes a reflector configured to redirect the optical radiation before it exits the optical blade.

20 Claims, 4 Drawing Sheets

(51) Int. Cl.
*B26B 21/40* (2006.01)
*B26B 21/56* (2006.01)
*B26B 21/58* (2006.01)
*A61B 18/00* (2006.01)
*A61B 18/22* (2006.01)

(56) References Cited

U.S. PATENT DOCUMENTS

| | | | | |
|---|---|---|---|---|
| 5,102,409 | A | * | 4/1992 | Balgorod ............ 606/5 |
| 5,182,857 | A | | 2/1993 | Simon |
| 5,423,803 | A | | 6/1995 | Tankovich |
| 5,606,798 | A | * | 3/1997 | Kelman ............ 30/41.5 |
| RE37,585 | E | | 3/2002 | Mourou |
| 6,699,236 | B1 | * | 3/2004 | Godfried et al. ............ 606/2 |
| 7,077,840 | B2 | | 7/2006 | Altshuler et al. |
| 7,582,082 | B2 | | 9/2009 | Van Hal |
| 2002/0103478 | A1 | | 8/2002 | Gwon |
| 2002/0125230 | A1 | | 9/2002 | Haight |
| 2002/0162360 | A1 | | 11/2002 | Schaffer |
| 2002/0172234 | A1 | | 11/2002 | Arisawa et al. |
| 2013/0018362 | A1 | * | 1/2013 | Verhagen ............ 606/9 |
| 2014/0296837 | A1 | * | 10/2014 | Varghese et al. ............ 606/9 |

FOREIGN PATENT DOCUMENTS

| | | |
|---|---|---|
| JP | 07287189 A | 10/1995 |
| JP | 10234459 A | 9/1998 |
| WO | 9305920 A1 | 4/1993 |
| WO | 9533600 | 12/1995 |
| WO | 0062700 A1 | 10/2000 |
| WO | 0100100 A1 | 1/2001 |
| WO | 2008058713 A1 | 5/2008 |
| WO | 2008115899 A2 | 9/2008 |
| WO | 2008120141 A2 | 10/2008 |

* cited by examiner

OPTICAL BLADE AND HAIR CUTTING DEVICE

FIELD OF THE INVENTION

The invention relates to an optical blade and a hair cutting device, preferably adapted for cutting a hair near skin of a human body part or animal body part. The invention also relates to a method of use for a hair cutting device.

BACKGROUND OF THE INVENTION

Document WO 2008/115899 A2 describes a compact and portable optical shaving device which cuts hair shafts using electromagnetic radiation. According to a preferred embodiment, the optical shaving device includes a power source that connects to one or more optical components. An optical device, such as an optical blade, can connect to and aligns with the array of optical components. The optical component(s) can provide light to the optics based on electrical energy from the power source. The optical component(s) or the optics can manipulate and direct the electromagnetic radiation to cut the hair shafts.

Classical shaving methods used commonly for the removal of facial and/or body hair employ certain selection means adapted for ensuring selective removal of hair whilst avoiding the potential risk of skin damage. For typical electrical shaving means, such as the common foil and rotating shaving systems, the selection means comprises a mechanical filter through which hairs can substantially penetrate and enter into the cutting chamber while skin is not able to substantially penetrate, avoiding excessive skin damage and irritation. In a rotating shaver, manipulation is preferably done by the shaving head and the cutting is preferably done by the knife. For blade shavers the selection means commonly comprise a mechanical arrangement with a combination of skin stretcher and gliding strip that limits the amount of skin exposure to the blade, while a spring system behind the knife effectively limits the local blade-skin interaction force to avoid cutting the skin. The means adapted for hair-skin selectivity comprised by the cutting mechanism actively limit the potential closeness of the shaving technique in order to balance the amount of acceptable skin irritation.

Conventional electrical shaving systems limit either the proximity of the cutting element to the skin, such as rotating/foil shavers, or limit the amount of force the blade exerts on the skin, such as blade shavers, in order to avoid accidental cutting of skin and skin irritation, nicks and cuts. The shaving process by these conventional shaving techniques typically comprises some or all of the following sub-processes: skin pre-treatment, skin manipulation, hair manipulation, hair refraction, hair cutting and skin post-treatment. There are many process variables that influence the desired outcome, these are amongst others: environmental conditions, such as humidity and temperature; device handling, such as speed, time, accuracy and pressure; device contour following capabilities and hair/skin properties.

The way in which each of the conventional shaving methods balances closeness and irritation depends strongly on its specific characteristics. In system blade shavers a number of sequentially passing blades each retract while cutting the hair, i.e. the blades pull the hair while cutting it. The next blade is then capable of cutting the hair at an even lower level, resulting in superior closeness. For rotating shaving, closeness is obtained through a combination of hair manipulation and hair retraction, together resulting in reasonable closeness. Foil shavers, lacking a clear means for hair refraction, rely mostly on a thin foil combined with skin and hair manipulation in order to achieve closeness.

For each of the methods described the amount of manipulation is limited due to the limitations imposed by the desire to maintain the integrity of the skin and to preserve the comfort during the shaving process. For instance, for blade shavers it is important to limit the amount of force required for hair cutting since otherwise the hair-pulling effect becomes highly uncomfortable, even though it might lead to improved closeness. For significant skin manipulation in, for instance, a foil or rotating shaving system, a high amount of local skin pressure is required which would result in extreme requirements for the force exerted by the device, and, hence, by the user on her/his skin, which would lead to excessive skin doming through holes and slots into the cutting chamber, resulting in skin irritation. The retraction means of rotating shaving systems is limited on account of the required acceleration of the hairs which is in the order of 1000 g and by the probability of correctly catching and retracting each hair.

However, a problem associated with each of the aforementioned techniques is that the processes of manipulation of hair and skin are performed with commonly the same means that are used to eventually cut the hairs, thus significantly limiting the amount of manipulation that can be employed, making the manipulation techniques sub-optimal. In addition, in each of the methods mentioned, the cutting process is non-optional, i.e. if an object is presented in front of a blade or inside the cutting chamber it will be cut, irrespective of whether it is actually being manipulated properly or whether it is a hair at all.

SUMMARY OF THE INVENTION

It is an object of the invention to provide a possibility for improving the balance of closeness versus irritation beyond the capabilities of conventional shaving systems, thereby allowing improved hair-skin manipulation in conjunction with optional hair cutting.

This object is achieved by the subject matter of the independent claims. Preferred embodiments are defined in the sub-claims.

According to a first aspect of the invention, this object is achieved by an optical blade, especially for use in a hair cutting device, comprising a blade body adapted for guiding optical radiation, and a tapered end adapted for allowing the optical radiation to exit the optical blade, wherein the tapered end comprises a reflector adapted for redirecting the optical radiation before it exits the optical blade.

The term "tapered end" refers to an end of the optical blade with a width that is tapered, preferably continuously tapered, i.e. the width of the blade body preferably becomes smaller along the blade direction. Different forms for the tapered end are possible, preferred embodiments of which are going to be described in the following. Such a tapered end preferably comprises the function to generate a local pressure towards a surface, such as a skin surface.

It is an idea of the invention to provide an optical blade adapted for an improved balance of closeness versus irritation by using an optional hair cutting mechanism, wherein the optical element, i.e. the optical blade, is brought into contact with skin of a human body part or animal body part and thus is adapted for manipulating a hair near skin in order to provide additional closeness beyond the capabilities of conventional shaving systems; since the tapered end of the optical blade is preferably blunt and, hence, not capable of inflicting skin damage, it is preferably adapted for manipulating skin at a local pressure beyond the skin safety limitations imposed on conventional techniques as well.

According to a preferred embodiment of the invention, the reflector is adapted for focusing the optical radiation, more preferably in front of the tapered end, such that the optical radiation is focused outside the optical blade. Preferably, the reflector is at least partially formed by a surface, more preferably by a curved surface, of the tapered end. It is worth noting that the optical radiation is preferably guided by the optical blade by means of reflection, preferably by means of total reflection. Further, it is noted that the term "reflection" refers to reflection of at least part of the optical radiation, i.e. a reflection smaller than 100% is also possible. According to a preferred embodiment of the invention, the curved surface of the tapered end comprises a convex, a concave, a parabolic and/or a grooved surface.

Further, according to a preferred embodiment of the invention, the tapered end comprises an exit window. The shape of the exit window is preferably flat. However, the shape can also be curved, convex, concave and/or zigzag.

According to a preferred embodiment of the invention, the reflector comprises a parabolic reflector, a non-spherical reflector, an elliptic reflector and/or a combination of a non-spherical focusing unit and a flat mirror reflector.

Furthermore, according to a preferred embodiment of the invention, the tapered end comprises a focusing unit which is adapted for focusing optical radiation at least partly perpendicularly to the surface of the focusing unit. Preferably, the focusing unit comprises a hollow cylindrical meniscus lens and/or a micro cylindrical lens. Preferably, the hollow cylindrical meniscus lens and/or the micro cylindrical lens are arranged near the exit window which preferably comprises a flat surface. The material of the optical blade preferably comprises glass, plastics and/or a semiconductor.

According to a second aspect of the invention, the above mentioned object is achieved by a hair cutting device, adapted for cutting a hair near skin of a human body part or animal body part, comprising an optical source, preferably a laser source, adapted for generating optical radiation for cutting the hair, and an optical blade according to the first aspect of the invention, wherein the optical source and the optical blade are arranged in such a way that optical radiation from the optical source is coupled into the blade body and is directed to the tapered end, and coupled out of the optical blade after reflection at the reflector.

The term "near skin" means preferably "on, above and/or below the skin". It goes without saying that the term "a hair near skin of a human body part or animal body part" preferably means that the hair protrudes from the skin surface of a human body part or animal body part and/or the hair is located on or somewhere below the skin surface.

According to a preferred embodiment of the invention, the material of the optical blade is transparent for a wavelength of optical radiation which is used for detecting the hair and/or for cutting the hair. Preferably, the optical blade further comprises a control unit adapted for regulating the local pressure on at least a part of the skin, when the hair cutting device is moved towards the skin. Preferably, the control unit comprises a spring system and/or a pressure sensor.

According to a preferred embodiment of the invention, the hair cutting device comprises a scanner adapted for guiding optical radiation coming from the optical source to a point along the optical blade. Preferably, the scanner is adapted for vibrating at least partly parallel to the exit window, such that a point outside the optical blade is addressed in a repeated fashion. Preferably, the scanner comprises a mirror, a focusing unit, a disc with a plurality of cylindrical focusing units and/or a focusing array with a plurality of cylindrical focusing units.

According to a third aspect of the invention, the above mentioned object is achieved by a method of use for a hair cutting device, adapted for cutting a hair near skin of a human body part or animal body part, the hair cutting device comprising an optical source, preferably a laser source, adapted for generating optical radiation for cutting the hair, and an optical blade comprising a blade body adapted for guiding the optical radiation generated by the optical source, and a tapered end adapted for allowing the optical radiation to exit the optical blade, wherein the optical source and the optical blade are arranged in such a way that optical radiation from the optical source which is coupled into the blade body is directed to the tapered end, and coupled out of the optical blade after reflection at the reflector, wherein the optical radiation exiting the hair cutting device is at least partly perpendicular to the optical radiation coupled into the blade body.

It is an idea of the invention to provide an optical blade, which preferably comes into contact with skin and hair. The optical blade is preferably adapted for manipulating the hair out of the skin and/or adapted for enabling hair cutting by means of a laser beam that is preferably guided to the tip of the optical blade at a level close to or beyond the original skin surface level relative to the hair. However, the optical blade can potentially be combined with an active manipulation means adapted for manipulating the hair out of the skin and/or adapted for enabling hair cutting by means of a laser beam that is preferably guided to the tip of the optical blade at a level close to or beyond the original skin surface level relative to the hair. The optical blade is preferably adapted for serving multiple functions: manipulating hair and skin and guiding and preferably focusing the cutting laser towards its target. A further function may be guiding and preferably focusing the detection laser towards its target.

Preferably, a detector is provided, which is adapted for detecting the presence of a hair in contact with or in close proximity to the optical blade, preferably enabling the cutting laser when a hair is detected, thereby making the cutting process optional and avoiding cutting skin that may preferably appear in front of the optical blade. Therefore, the manipulation mechanism and cutting unit are preferably decoupled from each other.

Preferably, the optical blade comprises an elongated blunt body, a skin-friendly skin-contact area and/or a light-exit area in close proximity to the skin-contact area. An optical focusing unit is preferably provided for defining an optical focus area, preferably for the hair detection light beam and/or for the hair cutting light beam relative to the light-exit area and/or the skin-contact area. The optical blade is preferably moved in operation over the skin surface and preferably pressed onto the skin surface, as a result of which the skin is then locally deformed by the skin-contact area and/or the hairs are manipulated, for instance by manipulation means, into an essentially upright position in front of the light-exit area. The hair cutting device preferably comprises an optical scanner that scans, preferably continuously, the hair detection light beam along the focus area. In addition, a hair recognition unit is preferably provided and is adapted for analyzing a signal provided by an optical detector which receives, via the optical blade, light reflected by the medium actually provided in a focus area. When the hair recognition unit detects specific optical properties indicating the presence of the hair, a hair cutting light beam is preferably activated and/or directed towards the position in the focus area where the hair is detected.

It has been found that when using the optical blade the focusing characteristics can be held nearly constant also in the presence of water, shaving additives and/or skin residues on or near the exit position where the laser beam exits the optical blade. For this purpose, preferably a hollow cylindrical meniscus lens at a position where the laser beam exits the optical blade, and a focusing structure which causes the rays of the laser beam to exit the meniscus lens in directions perpendicular to the meniscus lens surface are provided. In this way, the rays of the laser beam will not be refracted by the interface between the lens and the outside medium, so that any changes of the refractive index of the medium outside the optical blade do not affect the angle of incidence of the laser beam and the focus position. Preferably, the optical blade is manufactured by a moulding process as a monolithic lens comprising a relatively large and easy to manufacture non-spherical surface and a very small meniscus lens.

Furthermore, it is noted that the optical blade can provide for an accurate position of the focus in front of the light exit window of the tapered end. Preferably, this is achieved by a curved focusing surface of the optical blade arranged directly opposite to the exit window. In this way, a sufficient numerical aperture for hair cutting can be obtained.

The optical blade is preferably blunt. Further, the optical blade is preferably adapted for manipulating hair and skin such that a hair is at least partially separated from the skin and brought into contact with or in close proximity to the optical blade. Furthermore, the optical blade is preferably adapted for guiding and/or for focusing a light beam towards its front surface close to the skin for the purpose of detecting the presence of the hair. Moreover, the optical blade is preferably adapted for directing laser radiation, preferably appropriately focused laser radiation, towards the hair in order to effectuate the cutting process.

The hair cutting device preferably comprises a detector adapted for detecting the presence of an object in a focusing plane of the optical blade and adapted for discriminating optical properties of the object to assess whether the object is a hair with a high degree of probability or whether the object is actually something else like an immersion fluid, a bubble, a pimple, a freckle, a birthmark, a wrinkle or plane skin. The detector preferably comprises a control unit adapted for interpreting the signal arising from the detecting sensor to make said assessment, and to activate the cutting laser and/or to guide the cutting laser towards the correct position.

Moreover, an optical cutting source, such as a laser cutter, is preferably adapted for cutting a hair of all sizes, shapes and/or colors. Preferably, the optical cutting source is activated on demand at a local position along the length of the optical blade adapted for effectuating the cutting at a specific location.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

The optical blade according to the invention preferably comprises a number of different functionalities relating to its mechanical, geometrical and optical properties, which are going to be described in the following. According to a first preferred embodiment of the invention, the material of the optical blade is transparent to the wavelength of the light that is used for the detection unit as well as for the cutting unit. The material is preferably capable of withstanding the considerable intensity used in the cutting laser. In addition, it preferably does not introduce strong birefringence in order to avoid difficulties in the hair detection process. Depending on the wavelength of the light used, the optical blade is preferably manufactured from glass in any arbitrary shape using e.g. glass molding or diamond turning techniques or, according to other preferred embodiments of the invention, using specialty plastics, such as cyclo-olefin polymers combined with injection molding techniques.

According to the first preferred embodiment of the invention, the selected wavelengths of detecting and cutting light are entirely beyond 1 µm and thus the optical blade is preferably manufactured from semiconductor material, such as silicon, by means of various etching processes. According to other preferred embodiments of the invention, the selected wavelengths of detecting and/or cutting light are below 1 µm.

According to the first preferred embodiment of the invention, the optical blade shows an elongated dimension along the blade that determines the width of the skin treatment area. The width is preferably selected rather arbitrarily depending on the application. For instance, for the male beard area a preferred blade width of 30 to 50 mm is used, whereas for shaving of extremities and torso wider blades are preferred and for detailing in areas like the pubic region, but also for trendy shapes in facial hair management, a narrower applicator is preferably used.

Preferably, the cross sectional shape of the optical blade is such that it allows the light to enter on one side of the optical blade in a predetermined way and/or to exit at the surface closest to the cutting side of the blade in a convergent manner adapted for focusing at some distance from the surface. The optimal distance of the focus from the exit surface of the optical blade preferably depends on the means for detection and cutting of the hair, on the expected average and minimal hair thickness, and, hence, depends on the location on the body for which the shaver has been designed.

In order to make the light preferably converge in two directions, i.e. preferably both along the optical blade and perpendicular to it, the light entering the optical blade is preferably convergent in at least one direction along the blade, while the blade itself is preferably used for focusing in the direction at least partly perpendicular to the elongated blade direction.

Figure 1:
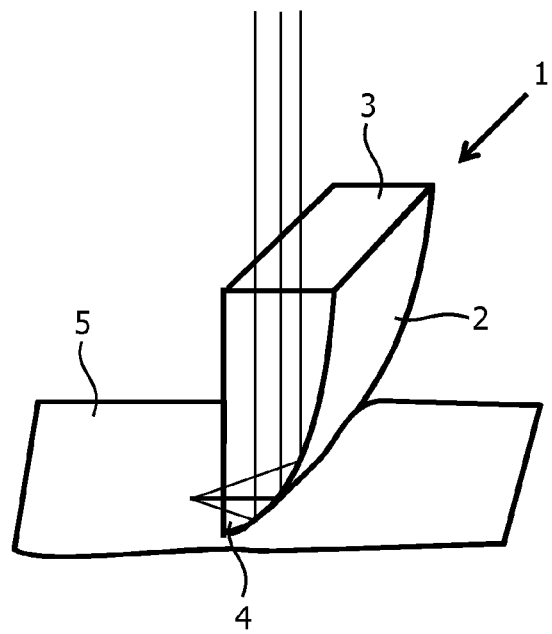
FIG. 1 illustrates internal reflection to deflect and focus the incident light to a point outside an optical blade according to a first preferred embodiment of the invention.

FIG. 1 shows an optical blade 1 with internal reflection to deflect and focus the incident light, indicated as solid lines, to a point outside the optical blade 1, the central direction of the light being parallel to a surface, such as the skin surface 5, according to the first preferred embodiment of the invention. The optical blade 1 comprises a blade body 3 and a tapered end 2, wherein the tapered end 2 comprises a parabolic reflector 4.

According to other preferred embodiments, the reflector comprises an elliptical reflector, in which light enters from the top, already pre-focused in the direction along the optical blade 1, which optical blade 1 itself preferably focuses and deflects the light to become substantially parallel to the skin surface 5. Reflective optical elements are preferred by virtue of their inherent achromatic characteristic, making them also suitable in cases where widely different wavelengths are preferably used for hair detection and/or for hair cutting.

Preferably, for a hair cutting device comprising a cutting unit and a detecting unit, it is desirable that the beam waist generated by the optical blade itself and the waist generated by a focusing unit which provides the focus along the direction of the optical blade substantially coincide. However, this is not obligatory. When the optical blade is in operation it will be preferably moved over the skin at least partly perpendicularly to its elongated axis, as in a conventional blade shaver, while a certain amount of local pressure is exerted on the skin. This local pressure is preferably ensured by a spring unit or by an active regulator, such as a pressure sensor, or by user feedback, i.e. the device switches off if insufficient or too much pressure is used. The local pressure strains the skin such that a hair protrudes more from the hair follicle than it would in the case of a fully relaxed skin. This is the case when the optical blade is moved against the local direction of hair growth, i.e. when the angle of the hair is such that the hair is tilted essentially upright instead of pushed down during the phase in which the optical blade contacts the hair.

Figure 2:
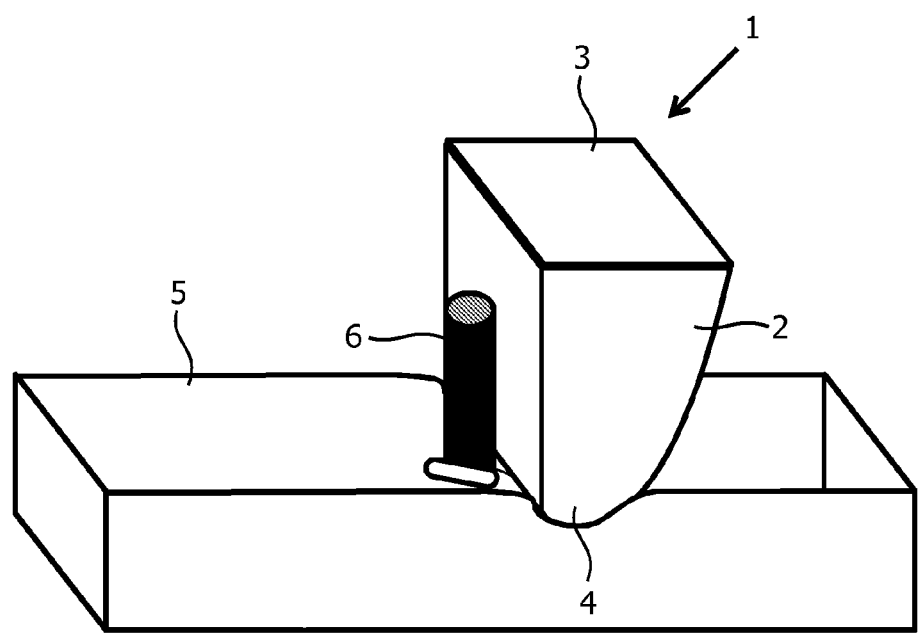
FIG. 2 schematically shows an optical blade brought into contact with skin and hair according to a second preferred embodiment of the invention.

FIG. 2 schematically shows the optical blade brought into contact with skin and hair according to a second preferred embodiment of the invention. The optical blade 1 indents the skin 5, thereby preferably providing access to the hair 6 at a level below the skin surface 5, providing an opportunity for cutting the hair 6 at a level that was originally below skin surface 5. According to the second preferred embodiment of the invention, an opportunity to detect the presence of a hair at the focus position of the optical blade 1 is provided. Further, an active hair manipulation means is preferably used to manipulate or retract the hair to achieve an even, close shave. For this purpose, serrated blade geometries are preferably used.

Once the hair 6 is cut and the skin surface 5 relaxes from the imposed strain, i.e. the optical blade 1 is removed, the hair 6 is preferably found to be cut closer to, and potentially below, skin surface 5. It is noted that if it is favorable for the purpose of hair-skin manipulation or if the cutting should be prevented from reaching the skin surface 5, an additional skin stretcher is installable in front of the optical blade 1 in order to stretch the skin and make the skin doming more predictable and to ensure that the cutting light remains parallel to and/or above the exposed skin area 5. Preferably, the skin stretcher additionally serves as laser beam deflector, whereby the light that reaches the stretcher is deflected upward and/or away from the skin surface 5 and is subsequently absorbed inside the hair cutting device.

It is noted that the outline of the optical blade does not necessarily coincide with the outline of the mechanical skin interface. If desired, mechanical means, for instance for the support of the optical blade or for skin manipulation, could be added. This makes the blade-skin interface preferably more comfortable and/or pleasant when used at a relatively high skin pressure.

When shaving against the direction of hair growth on the skin, the blade preferably positions the hair in a substantially upright position relative to the blade cross section. Once the base of the hair, i.e. the point where the hair enters the skin, comes into contact with the blade it will preferably be dragged along with the blade for a considerable amount of time. As a result the skin preferably gradually deforms and builds up sufficient stress to cause the hair to eventually bend underneath the blade. During this time the hair preferably sits conveniently in a detection plane of the optical blade, ensuring that sufficient time is available for the detection and/or the cutting of the hair, after which it will slide easily underneath the optical blade.

Figure 3:
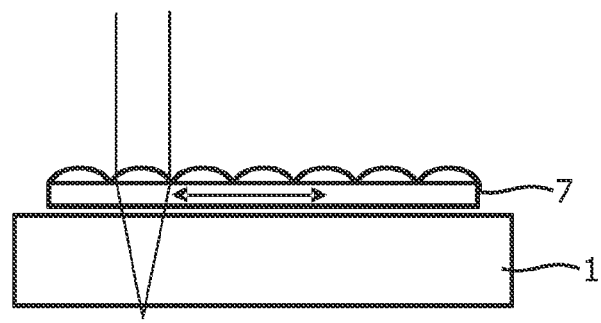
FIG. 3 shows a view along an optical blade direction demonstrating the use of an optical scanner comprising an array of cylindrical lenses according to a third preferred embodiment of the invention.

According to a third preferred embodiment of the invention, and as illustrated in FIG. 3, the use of a hair cutting device is now going to be described. A scanner 7 is used which is preferably adapted for ensuring that the convergent laser beam is addressed to each position along the optical blade 1. The scanner 7 comprises a scanning mirror and focusing unit combination that deflects a converging beam over the optical blade. A combination of optical blade 1 and scanner 7 corresponding to a lens array is shown in FIG. 3. The lens array is preferably vibrated in order to address every position along the optical blade 1 in a repeated fashion. According to other preferred embodiments of the invention, the scanner 7 comprises an array of cylindrical focusing units or a combination of an array of cylindrical focusing units with a scanning mirror to deflect a number of different beams simultaneously or sequentially over different areas of the optical blade.

All lenses are preferably illuminated simultaneously or the laser beam is preferably scanned over each lens sequentially at a repetition frequency much higher than the vibration frequency of the lens array. In order to preserve the achromatic behavior of the blade and/or scanner system, one can preferably opt for reflective optics instead of using the depicted refractive lens array.

According to other preferred embodiments of the invention, the elongated direction of the optical blade is curved, for instance to compensate for the cosine error in the case of a blade that vibrates at a single hinge point. In an extreme case the elongated axis could in fact be cylindrical, making the actual blade preferably coincide with the edge of a disc-shaped structure. A spinning disc preferably serves for scanning along the blade, wherein the spinning disc preferably comprises cylindrical focusing units arranged at its periphery. Each area of the circumference of the disc is preferably scanned N times per disc revolution, where N is the number of cylindrical lens units arranged on the disc periphery.

For hair detection efficacy, speed and/or specificity are important parameters. Methods for hair detection using Confocal Laser Scanning Microscopy, CLSM for short, have been described in the prior art and can be used in the embodiments of the invention, if desired, e.g. if birefringence of the optical elements should preferably be avoided. If the detection is preferably performed in the visible and NIR ranges of the spectrum, the use of either glass or suitable low-birefringence plastics is preferred. For the detection at longer wavelengths, glass or silicon is more suitable for the optical blade.

In order to make good use of the detection methods mentioned, it is preferred that the numerical aperture, i.e. the cone in which reflected light is collected from the detection target, is as high as possible and, additionally, immersion fluids are used in order to suppress spurious reflections returning from the skin surface. To obtain a high numerical aperture in the directions both parallel and perpendicular to the optical blade, it is made sure that the cylindrical lenses, as depicted in FIG. 3, are positioned as close as possible to the skin surface, so that the size of these elements remains small and thus the scan amplitude is maintained within reasonable bounds.

An anti-reflection coating for the specific wavelength is preferably used to avoid internal reflections at the exit face of the optical blade, or it is made sure that the refractive index of the immersion medium, such as the shaving additive, matches or exceeds the requirements to avoid internal reflections at the blade surface, while simultaneously being low enough to ensure sufficient reflection from hair. Typically, the refractive index is between that of water and glycerol in order to match the refractive index of the skin and/or not come too close to the refractive index of hair. It is clear that this is, for instance, obtained by many substances which are commonly used on skin, such as water, ultrasound gel, water-glycerol mixtures, different vegetable/mineral oils, such as baby oil and silicon oils, e.g. poly-dimethylsiloxane, as used in shampoos and conditioners and so on.

Figure 4:
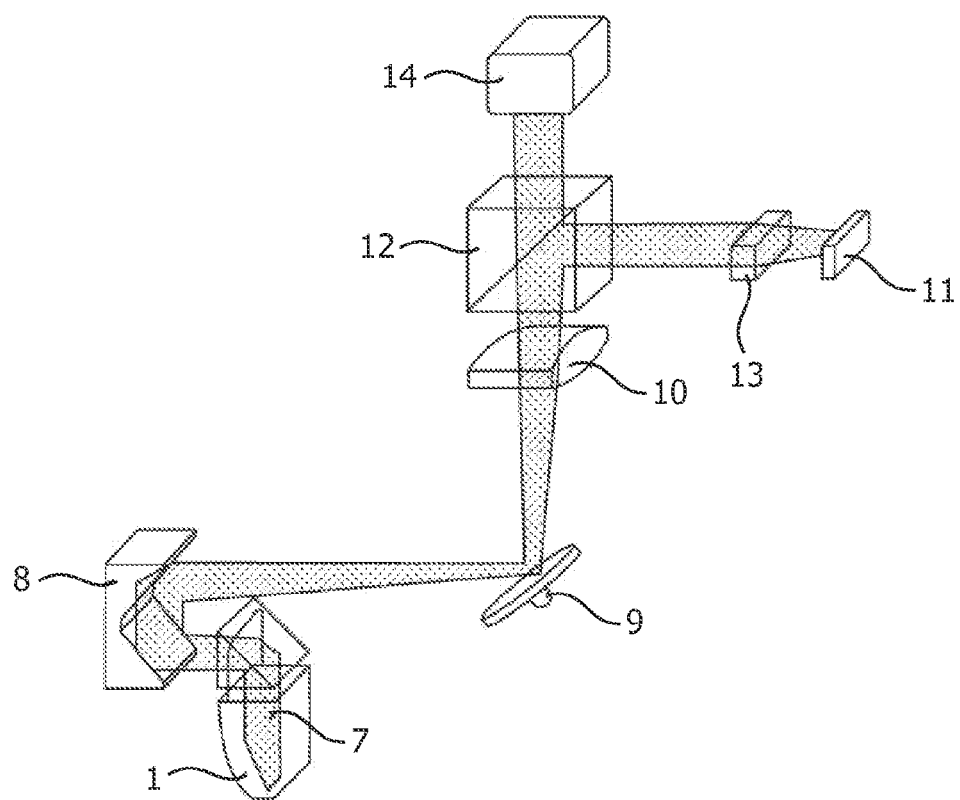
FIG. 4 shows a schematic layout of a setup for hair and skin imaging using an optical blade configuration according to a fourth preferred embodiment of the invention.

FIG. 4 shows a schematic layout of a setup for hair and skin imaging using an optical blade configuration according to a fourth preferred embodiment of the invention. Only one element of the cylindrical vibrating mirror, i.e. of the scanner 7, has been depicted for reasons of clarity. The laser beam path is indicated in a darker shade. The optical detection system implemented in an optical blade 1 preferably using CLSM is now going to be described.

Use is made of a vibrating lens/mirror array as an optical scanner 7, of which each element is preferably illuminated simultaneously by collimated laser light emanating from a collimating lens 8. According to other preferred embodiments, the collimating lens is replaced by a collimating mirror, or a combination of both is used. The light falling onto this collimating lens 8 preferably originates from a scanning micro-electromechanical mirror 9, MEMS mirror for short, that vibrates in a mode that is phase locked to the scanning motion of the lens array such that the same portion of the laser beam always addresses the same focusing element in the array. As a result, the beam in front of the MEMS mirror 9 does not need to be scanned, but has to be focused such that it generates the required beam shape on the collimating mirror 8 and/or fits appropriately inside the MEMS mirror aperture 9.

To this end, preferably focusing optics 10 have been inserted which are preferably adapted for converting the collimated laser beam appropriately. The signal returning from the optical blade 1 is in this way properly descanned and/or is imaged directly on a number of appropriately sized photodiodes 11 by means of a single beam splitter 12 and/or an equal number of lens elements in an array configuration 13.

In this way, it is arranged that each of the focusing units in the vibrating array 7 preferably projects its signal on one photodiode 11 at all times. If required, slits and/or pin-holes are easily added either in front of the photodiodes 11 or integrated in the MEMS scanning mirror 9. If more complex imaging requirements are to be considered, additional optics 14 are preferably placed behind the beam splitter 12 in order to separate different fractions of the returning light, for instance based on wavelength and/or polarization state of light, and/or the number of photodetectors are increased.

The signal returning from the photodiodes 11 is preferably interpreted based on the characteristic optical properties of a hair, and in that way it is possible to identify at each point in time which photodiode receives a signal due to hair and, hence, from which mirror array element the signal appears at what exact phase of the vibration of the array 7. This information is then preferably forwarded to the cutting mechanism adapted for cutting the hair at that specific location.

Depending on the hair cutter which is to be implemented in the optical blade shaving system, the detector preferably provides information with respect to either the center position or the peripheral edges of the hair relative to the elongated direction of the optical blade. In this way, the hair cutter, preferably a laser hair cutter, is aimed at the appropriate position for the cutting modality used. For instance, when the technique for cutting uses multiple very high repetition rate pulses or quasi-CW or CW irradiation, the control system preferably activates the laser when the scanner passes the initial edge of the hair and/or it needs to deactivate the laser when the scanner passes the final edge of the hair. For instance, when a single pulse is used for hair cutting, the control system provides an activation unit adapted for activating the cutting laser at a predetermined time during the scan such that the laser pulse more or less hits the center position of the hair to enable efficient cutting.

The hair cutting operation itself is preferably brought about by means of thermal effects, i.e. melting and/or evaporation, or by so-called laser ablative effects, whereby the material is preferably heated so rapidly that hardly any thermal residue or heat affected zone occurs on the remaining stubble and/or the cut part of the stubble does not become fused to the optical blade. According to other preferred embodiments of the invention, the cutting is brought about by means of laser induced optical breakdown, LIOB for short, in which isolated plasma is formed inside the hair, preferably causing shock waves and explosive bubble formation to effectuate the cutting of the hair from the inside out.

The processes for thermal cutting and for LIOB cutting are known in the prior art. Albeit for the implementation by means of an optical blade the usable wavelength ranges for these processes are preferably expanded to incorporate wavelengths that could potentially be harmful to the skin, since the optical blade is preferably designed such that the light is emitted substantially parallel to and/or away from the skin, potentially harmful effects are avoided.

Figure 5:
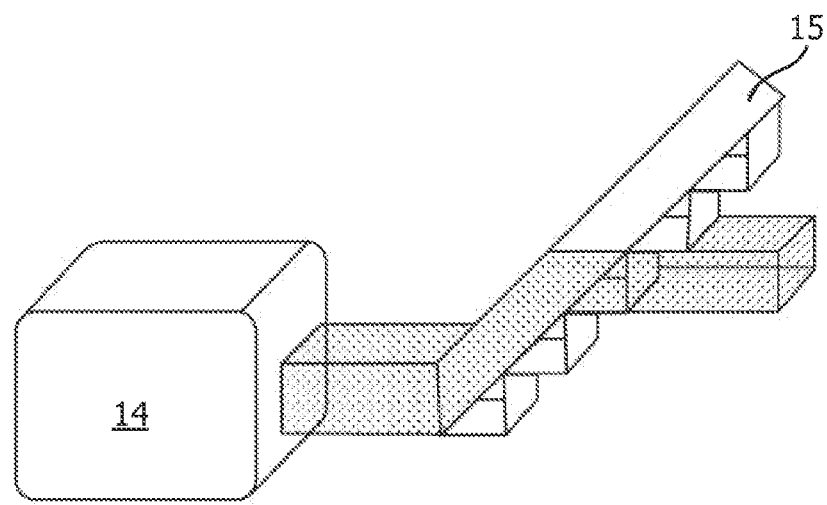
FIG. 5 shows an addressable optical switch adapted for directing a high power laser beam towards one of the scanning elements in an optical blade configuration according to a fifth preferred embodiment of the invention.

FIG. 5 shows an addressable optical switch adapted for directing a high power laser beam towards one of the scanning elements in an optical blade configuration according to a fifth preferred embodiment of the invention. In this switch each prism 15 is mounted on a piezo actuator which optionally drives the prism 15 in contact with the optical guide. By ensuring tight contact, the conditions for total internal reflection inside the optical guide are essentially broken and the laser beam is coupled out of the guide through the prism towards the corresponding lens/mirror element. For addressing the correct scanning lens or mirror element, use is preferably made of either a MEMS device or, according to other preferred embodiments of the invention, any means for fast digital addressing known, such as total internal reflection, TIR for short, laser beam addressing means 15 as shown in FIG. 5.

According to yet other preferred embodiments of the invention, combinations of the two are used, with coarse addressing being performed through the TIR device and more accurate aiming being ensured by means of the MEMS mirror. Preferably, the control unit either ensures that the proper prism is actuated to come into contact with the TIR beam guide before it activates the laser to generate a pulse or a series of pulses, or it uses the piezo actuators and TIR switch to act as a shutter of the mechanical Q-switch for the laser in order to effectuate the cutting process. In the latter case the TIR addressing means 15 is preferably placed inside the laser cavity.

According to other preferred embodiments of the invention, a cutting laser can be easily integrated in the detector described above. For instance, it is clear that between the beam splitter 12 and the focusing optics 10, as depicted in FIG. 4, plenty of space is made available to introduce an additional beam splitter for coupling in the light of the cutting system as generated by the system depicted in FIG. 5. In this way, the optical path of the detection and cutting unit is made such that they substantially overlap, thereby considerably reducing the risk of misfiring. Each one of the TIR prisms is made to correspond to one focusing unit and/or one detection photodiode combination, thus enabling very simple signal processing and/or interpretation, with the control unit making sure that no more than one piezo actuator is active at a time.

The invention shows potential for complete parallelization and/or ensures that full use is made of the elongated geometry of the optical blade. For instance, when wider or narrower blades are used, either the pitch of the lens elements and the amplitude of the vibrating scanning motion is increased or the number of scanning lenses and associated TIR prisms and detection circuits is to be increased, whichever is more favorable from a system architect's point of view.

In an optical-blade laser-shaver, an optical element in the form of a microcylindrical aspherical lens is integrated into an optical blade and brought into contact with skin and hair of a human or an animal body part according to a sixth preferred embodiment of the invention. The hair is a human beard hair according to the sixth preferred embodiment of the invention. In this way, a hair that is in close proximity to or in contact with the blade is preferably detected and/or cut by means of a laser beam emanating from the microlens. Preferably, the optical blade is insensitive to the type of shaving additive used and as such is also less sensitive to the shaving residue that is present at any time during the shaving process. In addition, compared to the complex miniature aspherical shape of the microlens, the invention improves the manufacturability of the optical blade by avoiding the need of these small aspherical features and preferably replacing them with spherical structures that are easier and more cost effective to manufacture.

Independent of the chosen cutting modality, an optical blade preferably comprises some form of optical focusing unit that is brought into contact with skin and hair and/or that allows cutting the hair close to the focusing unit.

Usually, the tip of a tapered end of an optical blade is in a very harsh environment involving different environmental conditions, such as the presence of skin/hair residue, different forms of additives, skin creams, water, sweat, sebum and so on. Each of the substances mentioned potentially leads to a different focusing behavior of the optical element due to their respective values of the refractive index. The sixth preferred embodiment of the invention shows a possibility to make the optical element insensitive to such variations while maintaining the general properties of the optical blade such as skin/hair manipulation, good light focusing quality and/or mechanical rigidity, respectively.

A further idea is to provide spherical surfaces that are preferably easy to miniaturize and thus a cheaper construction, since it is known that the manufacturing of miniature aspherical cylindrical optical elements is rather difficult and, hence, manufacturability of a single element aspherical tip is rather expensive. It is worth noting that the optical blade is preferably manufactured from any type of glass suitable for the selected wavelength and suitable for, for instance, precision moulding. This is in contrast to an optical element that relies on the refractive index difference between the glass and the immersion medium, i.e. the shaving additive, for providing the optical focusing power.

Figure 6:
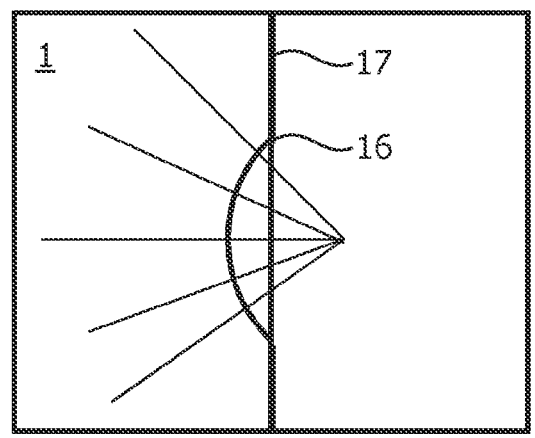
FIG. 6 shows a meniscus lens demonstrating the cylindrical shape and the direction of incident rays of light at right angles to the lens surface according to a sixth preferred embodiment of the invention.

FIG. 6 shows a meniscus lens 16 demonstrating the cylindrical shape and the direction of the incident rays of light at right angles to the lens surface according to the sixth preferred embodiment of the invention. A meniscus lens 16 is arranged at an exit window 17 which is preferably positioned at the tapered end of the optical blade 1. Therefore, the optical blade 1 is preferably isolated from its variable environment by means of a spherical cylindrical micro lens, which is a meniscus lens 16 in this embodiment. Such a lens is in essence a segment of a cylindrical tube, of which the center of rotation coincides with a beam waist position of the light incident on the surface of the lens.

From simple paraxial ray tracing optics, depicted in FIG. 6, it is clear that any changes to the refractive index of the medium outside the optical blade 1 will preferably not affect the angle of incidence and hence the power of the lens and/or the focus position of the light, respectively. This is due to the fact that all rays of light are incident at right angles to the surface of the meniscus lens 16 and therefore will not be refracted by the interface between lens and outside medium. The exit window 17 comprises a flat shape in this sixth preferred embodiment of the invention. Preferably, the exit window 17 is not arranged in front of the meniscus lens 16, otherwise the functioning of the meniscus lens 16 is at least partly bypassed.

Figure 7:
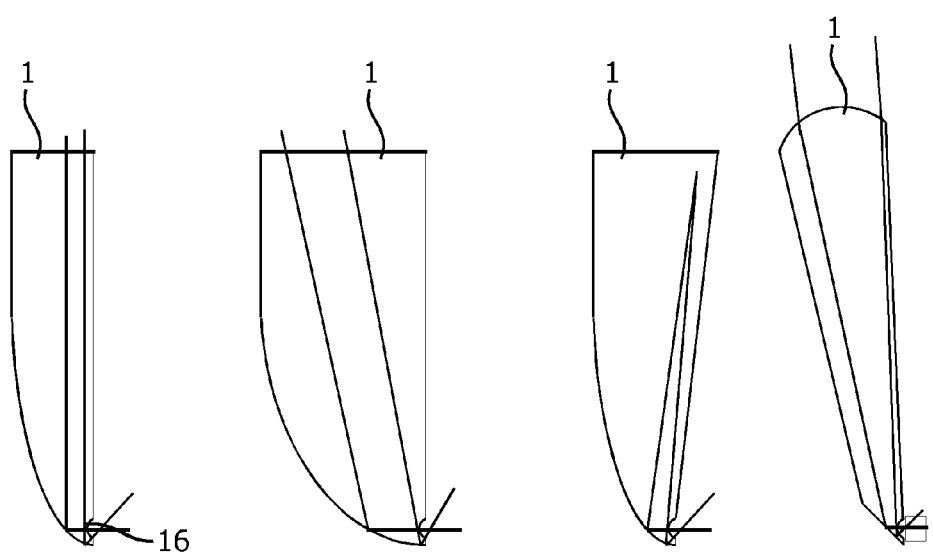
FIG. 7 shows different embodiments of a focusing unit with a meniscus lens used in an optical blade according to a seventh preferred embodiment of the invention.

FIG. 7 shows different possibilities of the focusing elements, which all incorporate a meniscus lens 16 which is used in an optical blade 1 according to the seventh preferred embodiment of the invention. From left to right: a parabolic reflector, a general aspherical reflector, an elliptical reflector, and a relatively low numerical aperture refractive reflector focusing by means of a combination of an aspherical lens and a flat mirror reflector, are illustrated in FIG. 7. Such focusing elements are preferably used for focusing the light at the geometrical center position of the meniscus lens 16. Close to the focus, the meniscus lens 16 preferably isolates the optical focusing surfaces from the harsh environment surrounding the tip of the optical blade 1, while being itself relatively insensitive to the various refractive index values of the materials surrounding and/or contacting it.

According to yet other preferred embodiments of the invention, the focusing element and the meniscus lens are constructed as an optical element comprising surfaces coated appropriately for reflecting and/or transmitting the light at the respective interfaces. This preferably leads to a monolithic lens design with relatively large and easy to manufacture aspherical surfaces and/or a very small meniscus lens structure, which is cylindrical and, hence, also relatively easy to produce when using, for instance, glass precision molding techniques, especially when compared to the construction difficulties encountered when making aspherical surfaces on this miniature scale. The construction of such an optical blade is preferably performed by creating an elliptically shaped mould whereby the small axes of the ellipse is at least partly perpendicular to the plane of the mould and the long axis is at least partly in plane with the mould. When the glass is poured, the surface of the glass that preferably sticks out of the mould after pouring is easily ground and/or polished to leave a non-critical flat surface. Then, a small cylindrical lens is easily ground and/or polished into the glass at the correct position before the glass is taken out of the mould to be post processed.

It is worth noting that using the geometries suggested preferably leads to the fact that the focusing is performed purely reflectively, making the lens construction intrinsically achromatic and/or independent of the actual type of glass used. The types of glass preferably selected are suitable for precision moulding while being highly transparent for all wavelengths that potentially are used, without requiring a very high refractive index for focusing into the surrounding high refractive index immersion medium. This is in contrast to optical blade geometries which employ an aspherical surface as the last optical interface.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A hair cutting device, configured to cut a hair near skin of a human body part or animal body part, comprising:
   an optical source configured to generate optical radiation for cutting the hair; and an optical blade,
   wherein the optical blade comprises a blade body configured to guide the optical radiation; a tapered end having a curved wall and an exit window with a flat shape configured to allow the optical radiation to exit the optical blade; and a straight wall meeting the curved wall of the tapered end and configured to contact the hair,
   wherein the tapered end comprises a reflector configured to redirect the optical radiation before exiting the optical blade through the exit window, and
   wherein the optical source and the optical blade are arranged in such a way that the optical radiation from the optical source which is coupled into the blade body is directed to the tapered end and coupled out of the optical blade after reflection at the reflector.

2. The hair cutting device of claim 1, wherein a material of the optical blade is transparent for a wavelength of optical radiation which is used for at least one of detecting the hair and for cutting the hair.

3. The hair cutting device of claim 1, further comprising a scanner configured to guide optical radiation coming from the optical source to a point along the optical blade.

4. The hair cutting device of claim 3, wherein the scanner is configured to vibrate at least partly parallel to the exit window, such that a point outside the optical blade is addressed in a repeated fashion.

5. The hair cutting device of claim 3, wherein the scanner comprises a mirror, a focusing unit, a disc with at least one of a plurality of cylindrical focusing units and a focusing array with a plurality of cylindrical focusing units.

6. The hair cutting device of claim 1, further comprising a detector configured to detect presence of the hair, wherein the optical source is activated in response to the detection of the presence of the hair.

7. The hair cutting device of claim 1, further comprising a detector configured to detect presence of the hair, wherein the optical radiation for cutting the hair is directed towards the detected hair.

8. The hair cutting device of claim 1, further comprising a detector configured to detect a presence of the hair, and a control unit configured to at least one of activate the optical source and guide the optical radiation towards a correct position of the detected hair in response to the detection of the presence of the hair.

9. The hair cutting device of claim 1, wherein the optical source, an optical focusing unit and the optical blade are arranged in such a way that the optical radiation from the optical source which is coupled into the blade body is directed to the tapered end and, after reflection at the reflector, is coupled out of the optical blade via the exit window into an optical focus area in front of the exit window, and
   wherein the tapered end of the blade body is arranged to be in contact with the skin during use and is blunt such as not to be capable of inflicting skin damage.

10. The hair cutting device of claim 1, wherein the optical blade further comprises a control unit configured to regulate a local pressure on at least a part of the skin, when the hair cutting device is moved towards the skin.

11. The hair cutting device of claim 1 wherein, prior to cutting the hair extending from a skin surface, the straight wall is further configured to hold the hair in a substantially perpendicular position relative the skin surface.

12. A hair cutting device for cutting a hair near skin of a human body part or animal body part, comprising:
   an optical source configured to generate optical radiation for cutting the hair; and
   an optical blade having a blade body configured to guide the optical radiation, and a tapered end configured to allow the optical radiation to exit the optical blade,
   wherein the tapered end comprises a reflector configured to redirect the optical radiation before exiting the optical blade,
   wherein the optical source and the optical blade are arranged in such a way that optical radiation from the optical source which is coupled into the blade body is directed to the tapered end and coupled out of the optical blade after reflection at the reflector, and
   wherein the optical blade further comprises a control unit configured to regulate a local pressure on at least a part of the skin, when the hair cutting device is moved towards the skin.

13. The hair cutting device of claim 12, wherein the control unit comprises at least one of a spring system and a pressure sensor.

14. An optical blade for use in a hair cutting device to cut hair, comprising:
   a blade body configured to guide optical radiation;
   a tapered end having a curved wall and an exit window with a flat shape configured to allow the optical radiation to exit the optical blade; and
   a straight wall meeting the curved wall of the tapered end and configured to contact the hair,
   wherein the tapered end comprises a reflector configured to redirect the optical radiation before exiting the optical blade through the exit window.

15. The optical blade of claim 14, wherein the reflector is configured to focus the optical radiation in front of the tapered end, such that the optical radiation is focused outside the optical blade.

16. The optical blade of claim 14, wherein the reflector is at least partially formed by a curved surface of the tapered end.

17. The optical blade of claim 14, wherein the reflector comprises at least one of a parabolic reflector, a non-spherical reflector, an elliptic reflector and a combination of a non-spherical focusing unit and a flat mirror reflector.

18. The optical blade of claim 14, wherein the tapered end further comprises a focusing unit which is configured to focus optical radiation at least partly perpendicularly relative to the surface of the focusing unit.

19. The optical blade of claim 18, wherein the focusing unit comprises at least one of a hollow cylindrical meniscus lens and a micro cylindrical lens.

20. The optical blade of claim 14 wherein, prior to cutting the hair extending from a skin surface, the straight wall is further configured to hold the hair in a substantially perpendicular position relative the skin surface.

\* \* \* \* \*